(12) United States Patent
Lofving et al.

(10) Patent No.: US 9,302,202 B2
(45) Date of Patent: Apr. 5, 2016

(54) CHROMATOGRAPHY COLUMN

(71) Applicant: GE HEALTHCARE BIO-SCIENCES AB, Uppsala (SE)

(72) Inventors: Per Lofving, Uppsala (SE); Mats Olsson, Uppsala (SE); Sven Wounder, Uppsala (SE); Jerker Persson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 54 days.

(21) Appl. No.: 14/295,690

(22) Filed: Jun. 4, 2014

(65) Prior Publication Data
US 2014/0284260 A1    Sep. 25, 2014

Related U.S. Application Data

(60) Continuation of application No. 12/250,569, filed on Oct. 14, 2008, now Pat. No. 8,778,188, which is a division of application No. 11/183,522, filed on Jul. 18, 2005, now Pat. No. 7,452,464.

(30) Foreign Application Priority Data

Nov. 2, 2004  (GB) .................................. 0424259.0

(51) Int. Cl.
*B01D 15/22*     (2006.01)
*G01N 30/60*     (2006.01)
(52) U.S. Cl.
CPC ............ *B01D 15/22* (2013.01); *G01N 30/6004* (2013.01); *G01N 30/6047* (2013.01); *Y10T 29/49819* (2015.01)

(58) Field of Classification Search
CPC ............... B01D 15/22; G01N 30/6047; G01N 30/6004; Y10T 29/49819
USPC .............. 210/635, 656, 659, 198.2, 241, 269, 210/456; 96/101
See application file for complete search history.

(56) References Cited

U.S. PATENT DOCUMENTS 4,204,960 A    5/1980 Sugiyama et al.
4,262,447 A    4/1981 Schneier et al.
(Continued)

FOREIGN PATENT DOCUMENTS

WO         82/01661       5/1982
WO         WO82/01661     5/1982
(Continued)

OTHER PUBLICATIONS

JP Utility Model Appln. No. 57-066872 (JP58-169562U (Nov. 12, 1983)).

*Primary Examiner* — Ernest G Therkorn
(74) *Attorney, Agent, or Firm* — Parks Wood LLC

(57) ABSTRACT

A chromatography column having a longitudinal axis and comprising a column wall with a first end and a second end, a first end plate assembly removably connectable to said first end of the column wall, a second end plate assembly removably connectable to said second end of the column wall, wherein said first end plate assembly, said column wall and said second end plate assembly are arranged along the longitudinal axis of the column wherein the column wall, and/or first end plate assembly and/or second end plate assembly is/are rotatable about an axis of rotation wherein said axis of rotation is parallel to the longitudinal axis of said column and positioned outside the column.

5 Claims, 13 Drawing Sheets

(56) References Cited

U.S. PATENT DOCUMENTS

| | | |
|---|---|---|
| 4,769,141 A | 9/1988 | Couillard |
| 4,891,133 A | 1/1990 | Colvin, Jr. |
| 5,217,608 A | 6/1993 | Conway |
| 5,470,479 A | 11/1995 | Snyder et al. |
| 5,667,675 A | 9/1997 | Hatch et al. |
| 6,074,556 A | 6/2000 | Van Davelaar |
| 6,117,317 A | 9/2000 | Dickson et al. |
| 6,123,849 A | 9/2000 | Purdom |
| 6,740,241 B1 | 5/2004 | Dickson |
| 6,979,402 B1 | 12/2005 | Sprague et al. |
| 7,041,216 B2 | 5/2006 | Dunkley et al. |
| 7,238,282 B2 | 7/2007 | Perreault et al. |
| 7,452,464 B2 * | 11/2008 | Uselius et al. ............. 210/198.2 |
| 8,778,188 B2 * | 7/2014 | Uselius et al. ................ 210/656 |
| 2002/0153321 A1 | 10/2002 | Prior et al. |

FOREIGN PATENT DOCUMENTS

| | | |
|---|---|---|
| WO | 00/00259 | 1/2000 |
| WO | WO00/00259 | 1/2000 |
| WO | WO 03/076923 | 9/2003 |

* cited by examiner

CHROMATOGRAPHY COLUMN

CROSS-REFERENCE TO RELATED APPLICATIONS

This application is a continuation of U.S. patent application Ser. No. 12/250,569 filed Oct. 14, 2008, now U.S. Pat. No. 8,778,188, which is a divisional of U.S. patent application Ser. No. 11/183,522 filed Jul. 18, 2005, U.S. Pat. No. 7,452,464, which claims priority to application number 0424259.0 filed in Great Britain on Nov. 2, 2004.

FIELD OF THE INVENTION

The present invention relates to chromatography columns of the type mentioned in the preambles of the independent claims.

BACKGROUND OF INVENTION

Chromatography columns may be used in industrial process to purify process liquids and separate substances of interest from process liquids. Prior art chromatography columns comprise a column wall in the form of hollow column tube which is connected to a removable upper end plate assembly and a removable lower end plate assembly. One end plate assembly is provided with a process fluid inlet arrangement, typically comprising an inlet pipe and an inlet valve and the other end plate assembly is provided with a process fluid outlet arrangement, typically comprising an outlet pipe and an outlet valve. Each end of the column tube is usually provided in the interior of the column with a removable distribution system. These inlet and outlet distribution systems may be attached to the respective end plate assembly or the upper distribution system may be arranged to be movable towards or away from the end plate assembly. During use, the space in the column between the distribution systems is usually filled with a chromatography medium. If necessary a retaining mesh may be provided between each distribution system and the media. The inlet distribution system is intended to distribute incoming fluid evenly over the surface of the media at the inlet end of the column while the outlet distribution system is intended to collect fluid evenly from the surface of the media at the outlet end of the column Such a column may weigh several tonnes. Typically the end plate assemblies are bolted to flanges provided at each end of the column Alternatively the end plate assemblies may be connected by longitudinal tie bars. Seals are usually provided between the end plates assemblies, inlet and outlet pipes, distribution systems and valves in order to prevent leakage. Columns are typically provided with legs to raise the lower end plate assembly off the ground in order to provide access to the lower end plate assembly, the inlet or outlet pipe and the valve arrangement. When such a column requires maintenance to, or cleaning of, internal components, such as the valves, seals, distribution systems, etc. lifting gear such as a crane is necessary to lift the upper end plate assembly off the column tube and the column tube off the lower end plate assembly.

SUMMARY OF THE INVENTION

According to the present invention, at least some of the problems with the prior art are solved by means of a device having the features present in the characterising part of claim 1.

BRIEF DESCRIPTION OF THE FIGURES

FIG. 1b shows a plane view from above of the column of FIG. 1a.

DETAILED DESCRIPTION OF THE INVENTION

Figure 1A:
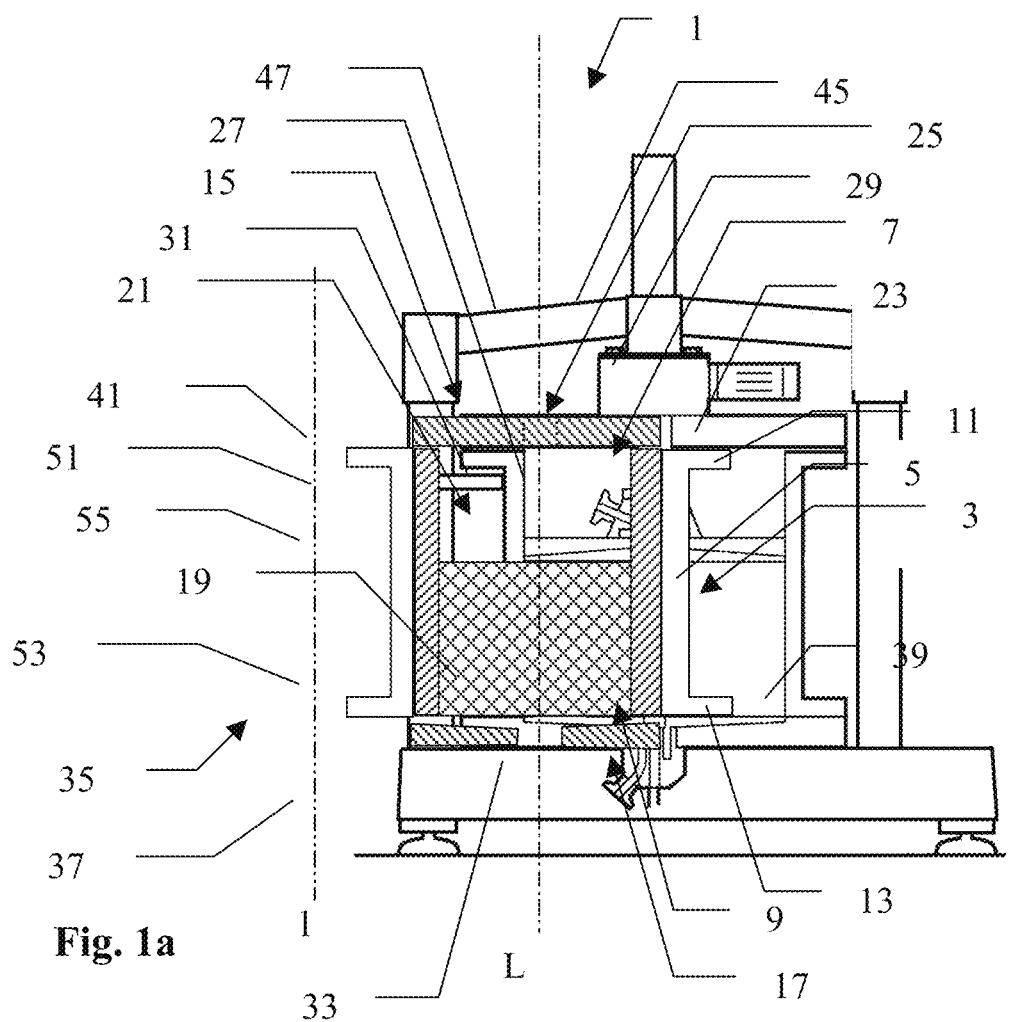
FIG. 1a shows a partial cross-sectional view of a first embodiment of a chromatography column in accordance with the present invention.

FIGS. 1-5 show a first embodiment of a chromatography column 1 in accordance with the present invention. Column 1 comprises a hollow column wall 3, which in this embodiment is in the form of a cylinder 5, with a first open end 7 and a second open end 9. Each open end 7, 9 is provided with an outward projecting circumferential flange 11, respectively 13, arranged perpendicular to the longitudinal axis L of the column wall 3. A first end plate assembly 15 is removably fastened to flange 11 and a second end plate assembly 17 is removably fastened to flange 13. In this embodiment of the present invention the column is intended to be used in the down-flow mode, i.e.

the first end plate assembly 15 is intended to be used to feed fluids to the column 1 and the second end plate assembly is intended to be used to remove fluids from the column, however the present invention is equally applicable to columns using the up-flow mode. In use, column wall 3 may be occupied by a chromatography medium 19. First end plate assembly 15 is provided with the usual fluid feed system 21 (also called "movable adapter") comprising one or more valves, distribution channels, distribution nets, nozzles, connectors, etc which are well-known in the art and which are referenced collectively under the reference number 21. In this example of a column, first end plate assembly 15 comprises first end plate 23 which is removably fastenable to flange 11, and which has a central opening 25 through which a hollow shaft 27 is movable in the longitudinal direction of the column by a motor 29. In use, hollow shaft 27 projects into the column cavity 31 and supports the fluid feed system. Motor and drive assembly 29 can be used to move the movable adapter 21 towards and away from first end plate 23 and thereby adjust the depth of movable adapter 21 in the column 1. Second end plate assembly 17 is provided with the usual fluid collecting system 33 comprising one or more valves, distribution channels, distribution nets, nozzles, connectors, etc. which are well-known in the art and which are referenced collectively under the reference number 33.

Column 1 is supported in frame 35. Frame 35 comprises feet 37 in contact with the ground. Feet 37 support three extendable legs 39, 41, 43 which extend upwards and are each provided with a substantially horizontal arm 45, 47, 49. Arms 45-49 pass over the column 1 are attached to end plate 23. Extendable legs 39-43 provided with lifting means such as jacks or rams arranged to be able to lift arms 45-49 and the first end plate 23 sufficiently high enough so that when movable adapter 21 has been raised to its closest possible position to the underside of first end plate 23 it is possible to raise the first end plate assembly 15 so that none of it is inside the column wall 3.

Column wall 3 is attached to leg 41 by a pair of arms 51, 53 which are mounted on a sleeve 55 on leg 41. Sleeve 55 is rotatable around leg 41 and is also movable along the longitudinal axis "1" of leg 41.

Figure 1B:
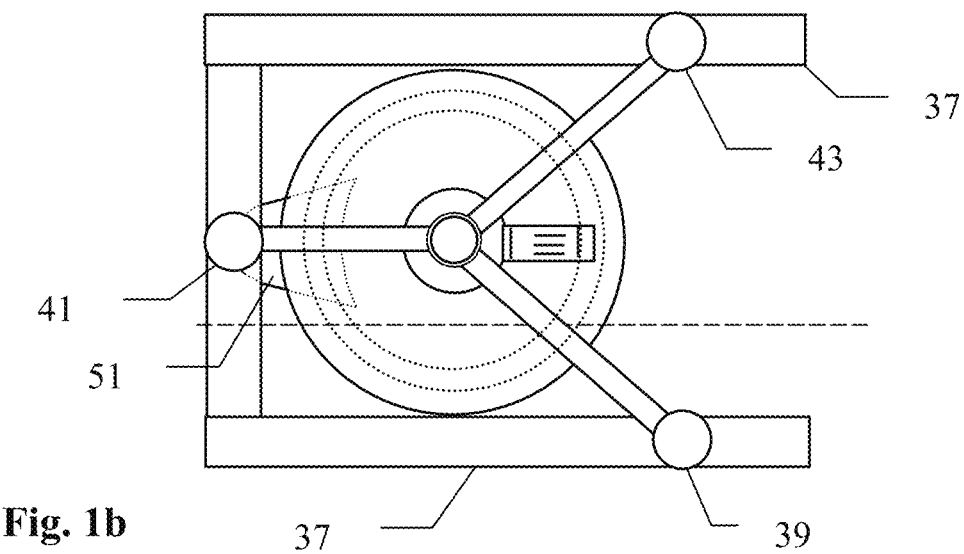

FIGS. 1a and 1b show the chromatography column in the normal operating condition with first and second end plates sealed against the ends of column wall.

Figure 2:
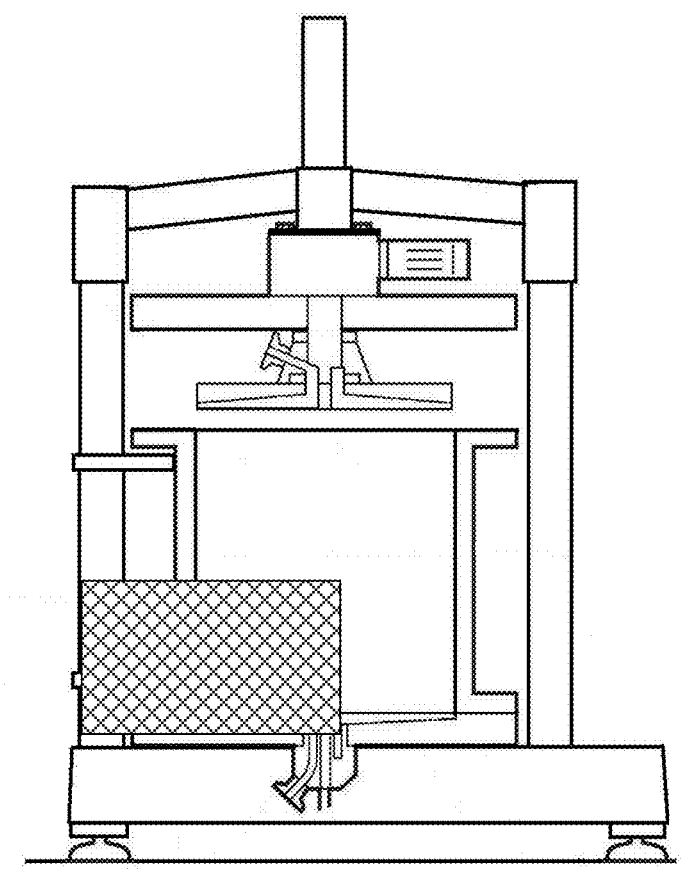
FIG. 2 shows a view corresponding to that of FIG. 1a wherein the first end plate and distribution system have been raised above the column wall.
Figure 3:
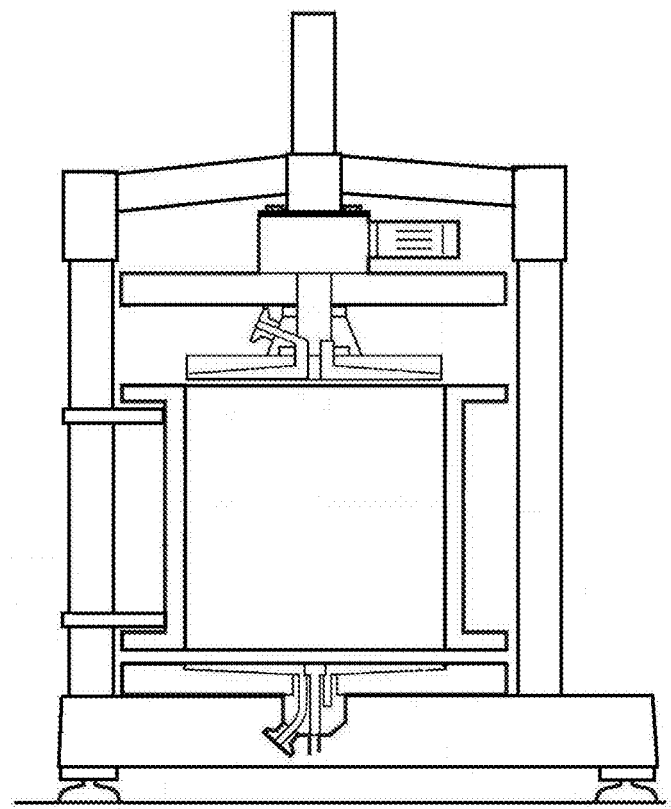
FIG. 3 shows a view corresponding to that of FIG. 2a wherein the first end plate and distribution system have been raised above the column wall, and the column wall has been raised above the second end plate.
Figure 4:
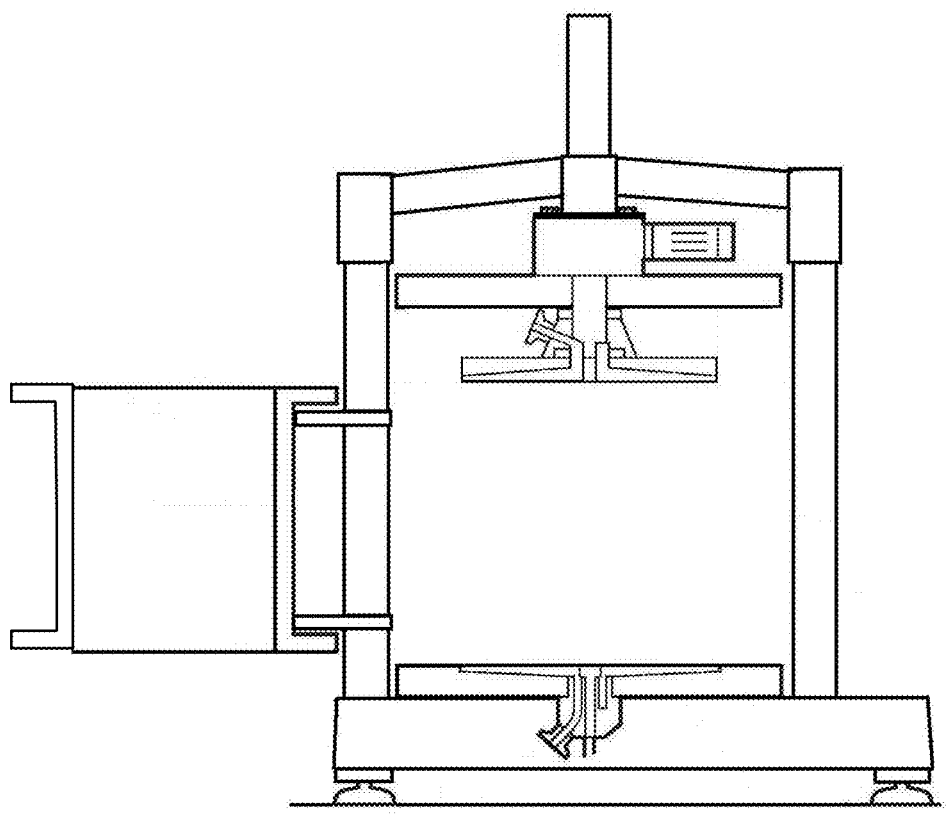
FIG. 4 shows a view corresponding to that of FIG. 3 wherein the first end plate and distribution system have been raised above the column wall, and the column wall has been raised above the second end plate and rotated out from a position between the first and second end plates.

FIGS. 2-4 shows stages in rearranging the column allow access to the distribution systems and end plates.

In FIG. 2, the column is shown after it has been emptied of media and fluids, movable adapter 21 has been raised by motor until the movable adapter 21 is close to the bottom of first end plate assembly and then first end plate has been unfasten from the top of column wall and raised by means of extendable legs 39-41 so that the lowest part of movable adapter 21 is above the top of cylinder wall.

In FIG. 3, the column is shown after column wall has been detached from second end plate assembly and sleeve 55 has been raised along the longitudinal axis "1" of 41 so that none of movable adapter 21 or second end plate assembly is inside the cylinder wall.

FIG. 4 shows the column after the cylinder wall has been rotated about axis "1" so that the column wall is no longer positioned between the first and second end plate assemblies.

Figure 5:
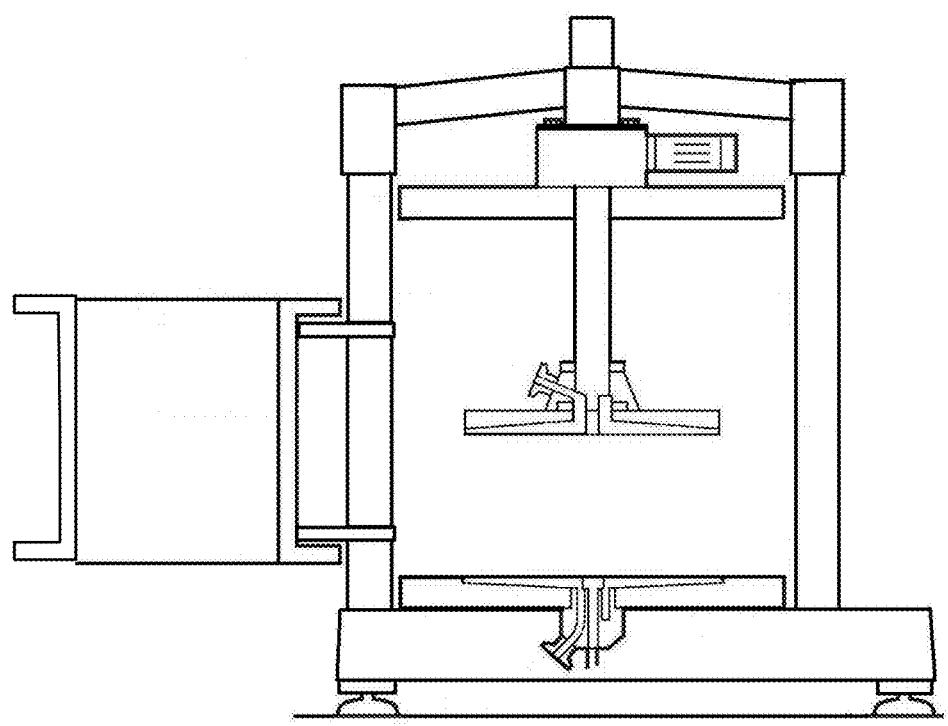
FIG. 5 shows the column after the feed system has be relowered in order to allow easy access to it.

FIG. 5 shows the column after the movable adapter has be relowered in order to allow easy access to it.

Figure 6:
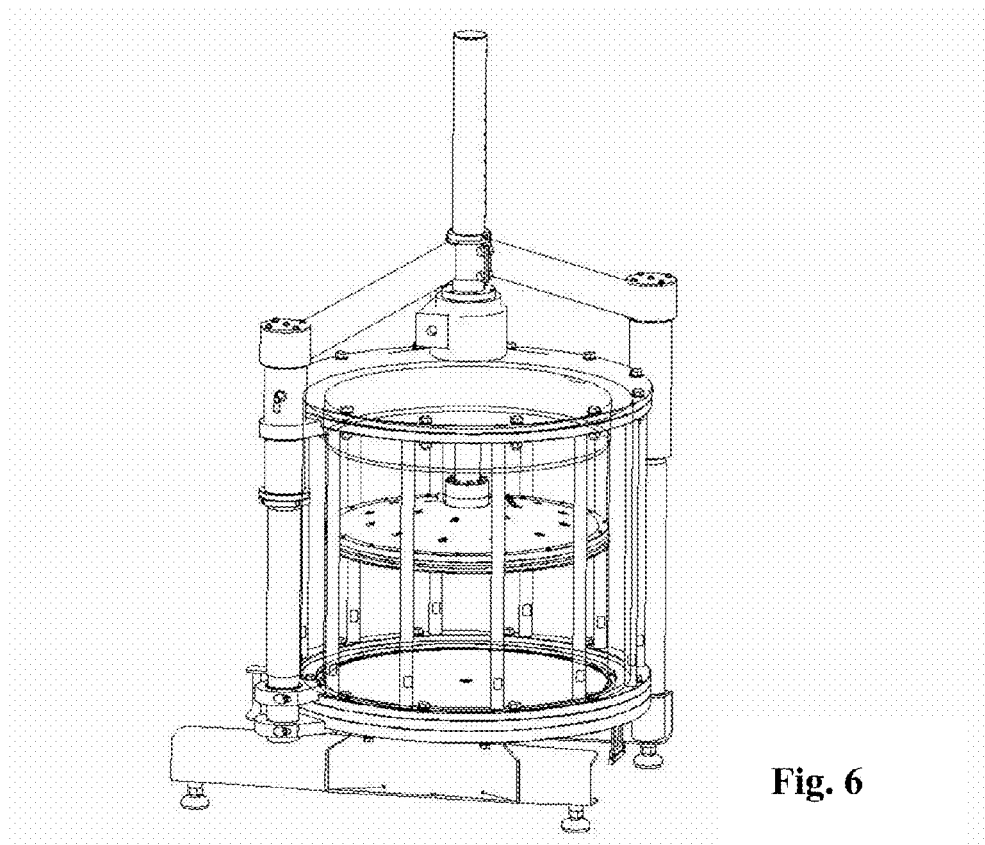
FIG. 6 shows a perspective view of a second embodiment of the present invention having only 2 extendable legs.

FIG. 6 shows a perspective view of a second embodiment of the present invention having only 2 extendable legs.

Figure 7:
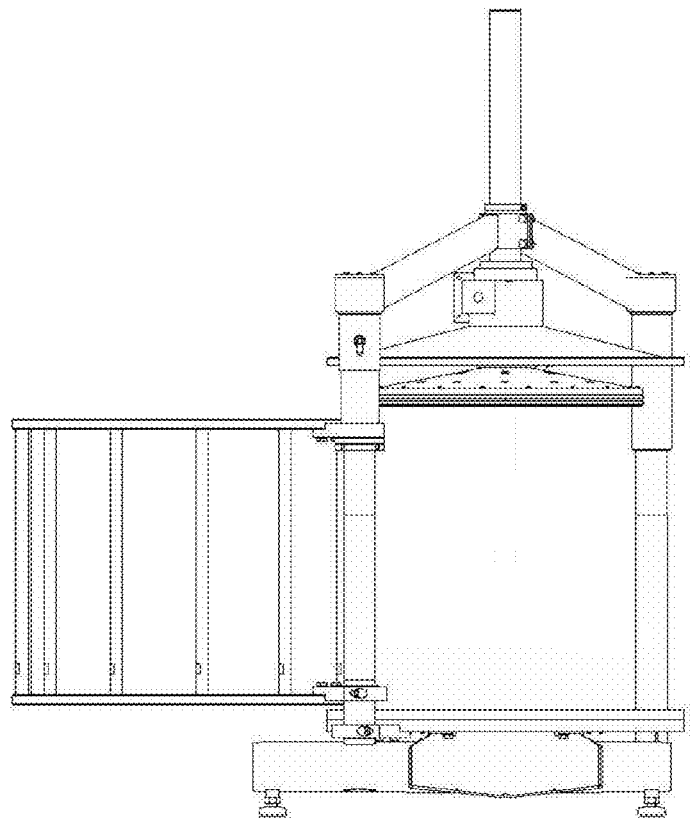
FIG. 7 shows a side view of the column of FIG. 6 with the cylinder wall in a position corresponding to that of FIG. 4.

FIG. 7 shows a side view of the column of FIG. 6 with the cylinder wall in a position corresponding to that of FIG. 4.

FIGS. 8-14 show lateral views of a third embodiment of a column in accordance with the present invention. In this embodiment of a column, the column has two-legs 339, 341 and is adapted so that the movable adapter lifting means such as motor and drive assembly 329 for the movable adapter 321 is able to be used for extending the legs 339, 341. Thus no jacks or rams are needed to extend the column legs 339, 341. In order to achieve this upper end of the column wall 303 is provided with at least one movable adapter locking pin 371 able to be moved to and from locking engagement with a locking bore 373 arranged on movable adapter 321. Preferably the locking pin 371 and locking bore 373 are arranged so that locking pin 371 is able to be moved into locking bore 373 when the movable adapter has been raised to substantially its uppermost position. When locking pin(s) is/are in locking engagement with movable adapter 321 relative movement between movable adapter 321 and the column wall 303 is prevented.

Legs 339 and 341 are each provided with an upper telescopic shaft locking pin 375 able to be moved to and from a position where it prevents movement of telescopic shafts 379 which are slidably arranged in the upper portions of legs 339, 341.

Preferably the locking pins 375 are arranged so that locking pins 375 are able to be moved into locking position when the telescopic shafts 379 has been raised to substantially their most extended positions, thereby locking telescopic shafts 379 in the raised position.

Leg 341, which supports column wall arms 351, 353, is provided with a locking hole 381 into which a locking pin 383 mounted on arm 353 may be moved into and out of locking engagement. Preferably the locking pin 383 and locking hole 381 are arranged so that locking pin 383 is able to be moved into locking hole 381 when the column wall 303 has been raised to a position where it is no longer in contact with second end plate assembly 317.

The following description and FIGS. 8-14 describe and illustrate the steps of a method in accordance with the present invention for rearranging the components of a column in order to allow the column wall 303 to be rotated to a position where it is no longer between the column legs 339, 341.

Figure 8:
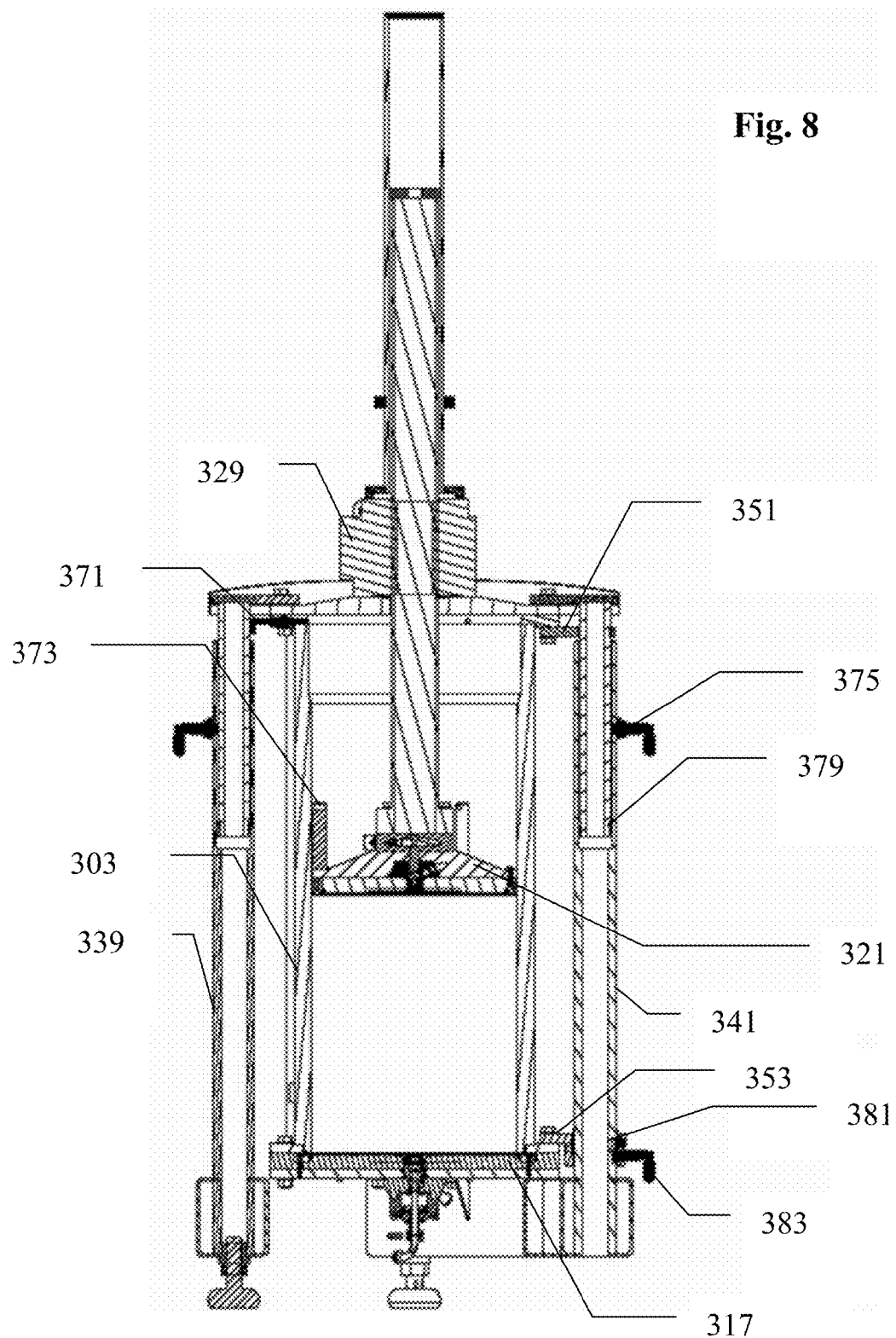
FIGS. 8-14 shows lateral views and cross-sections of a third embodiment of the present invention.

FIG. 8 shows a column 301 in its normal operating position with the movable adapter 321 in a possible working position inside column wall 303 and telescopic shafts 379 retracted.

Figure 9:
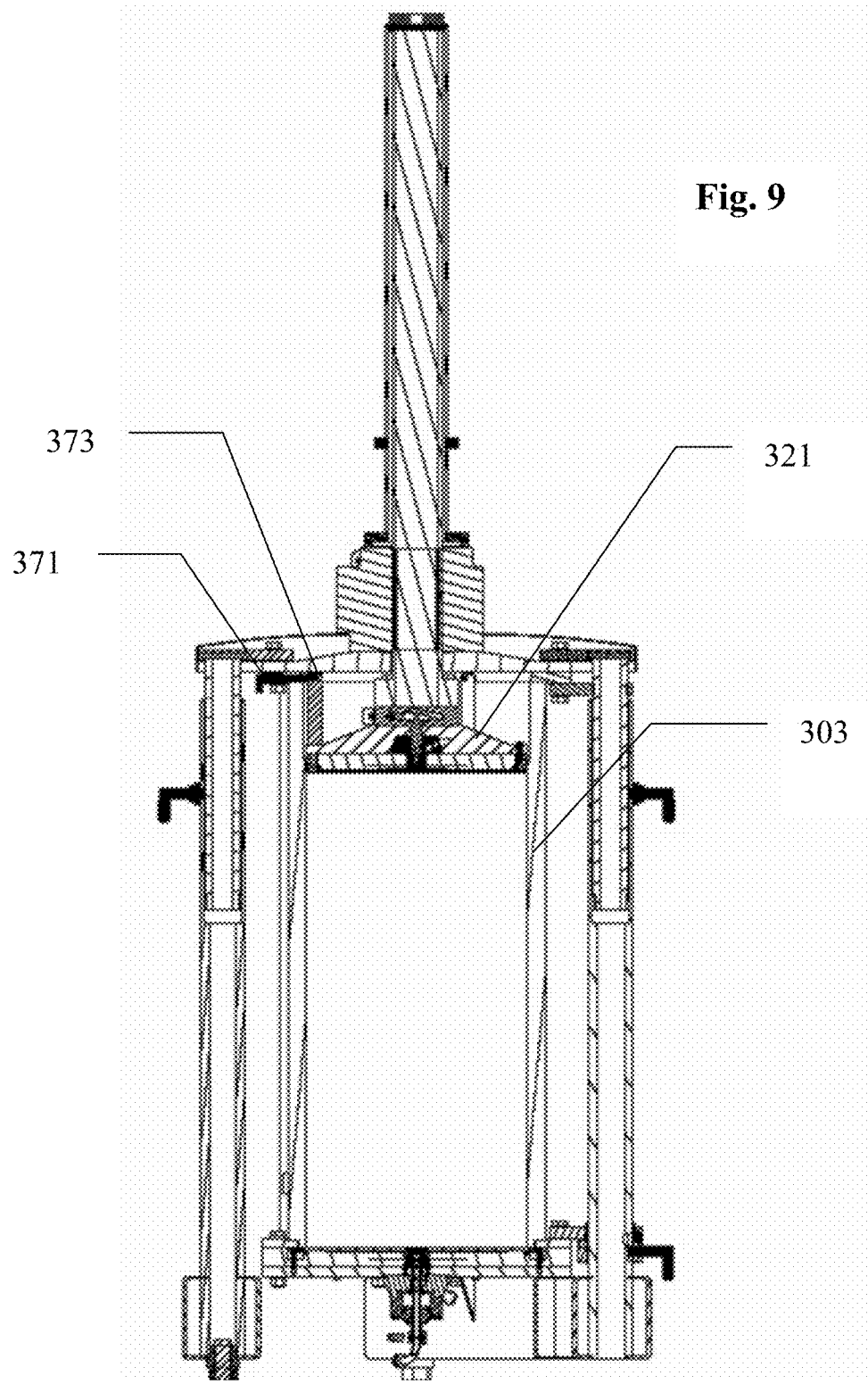

FIG. 9 shows a first step in the method in which the movable adapter lifting means 329 has raised the movable adapter 321 to substantially its uppermost position and movable adapter locking pin 371 has been slid into engagement with locking bore 373 thus preventing further relative movement between movable adapter 321 and column wall 303.

Figure 10:
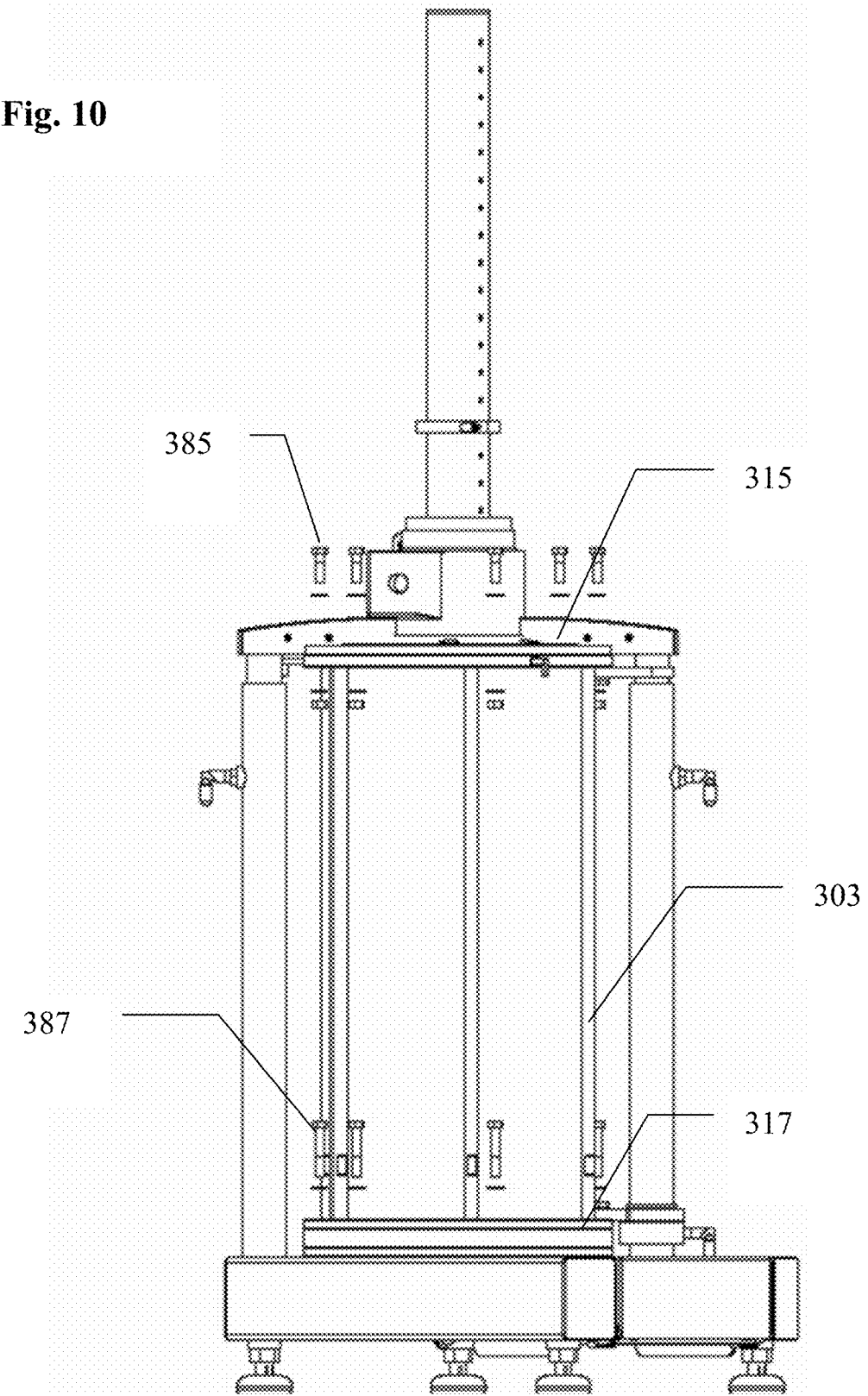

FIG. 10 shows the next stage in the method in which the removable fastening means such as bolts 385 for releasably fastening first end plate assembly 315 to the upper end of column wall 303 and bolts 387 for releasably fastening second end plate assembly 317 to the lower end of column wall 303 have been unfastened and removed.

Figure 11:
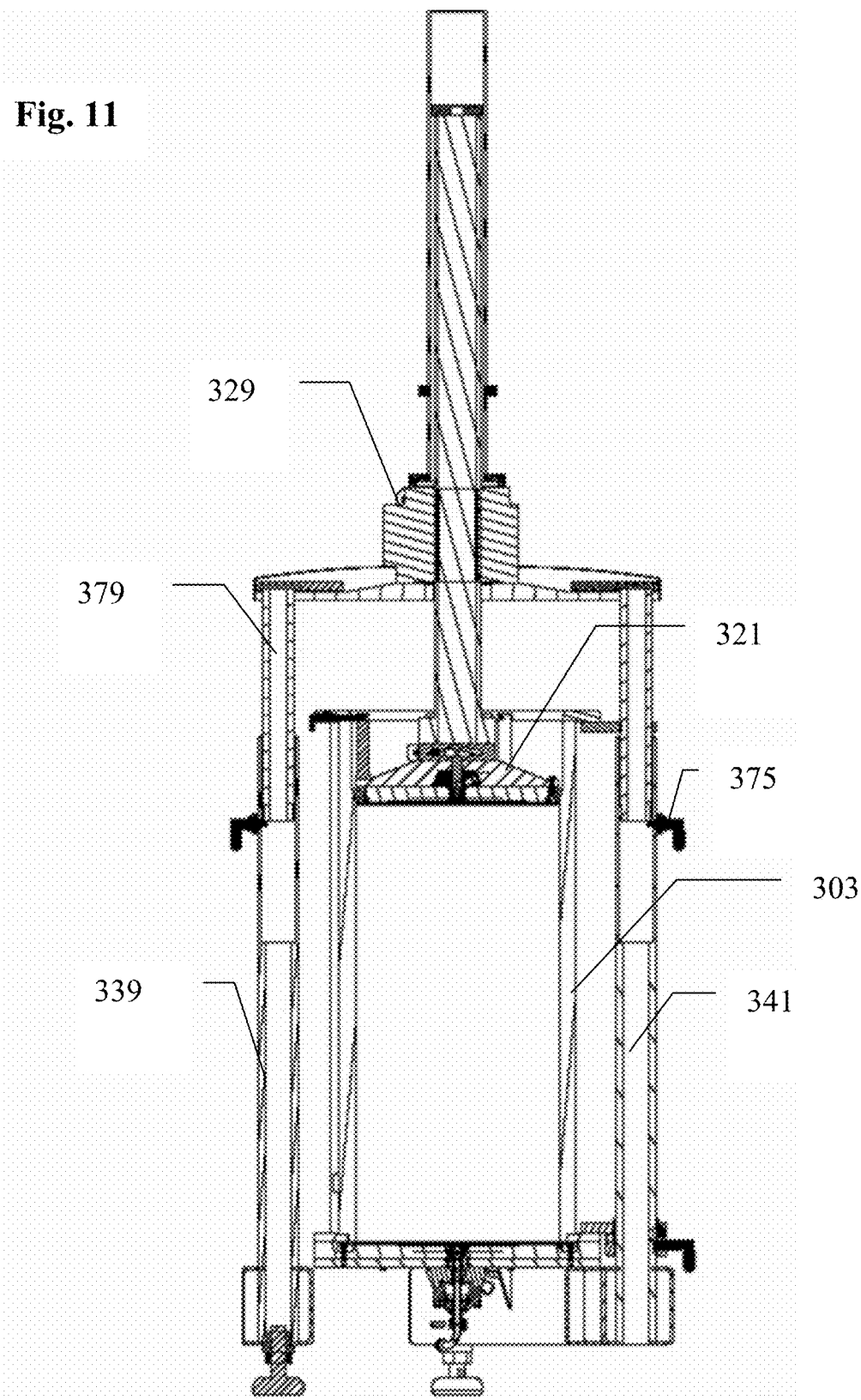

FIG. 11 shows the next stage in the method in which movable adapter lifting means 329 has been actuated in the way which during normal operation would cause the movable adapter to be moved downwards. However, as movable adapter 329 is locked by locking pin 371 and locking bore 373 to column wall, it is not possible for movable adapter 329 to descend—instead first end plate assembly 315 and all the column components rigidly attached to it such as telescopic shafts 379 and movable adapter lifting means 329 are raised. This movement is continued until telescopic shafts 379 have been extended sufficiently far so as to allow telescopic shaft locking pins 375 to be moved into position which prevent the telescopic shafts 379 being lowered.

Figure 12:
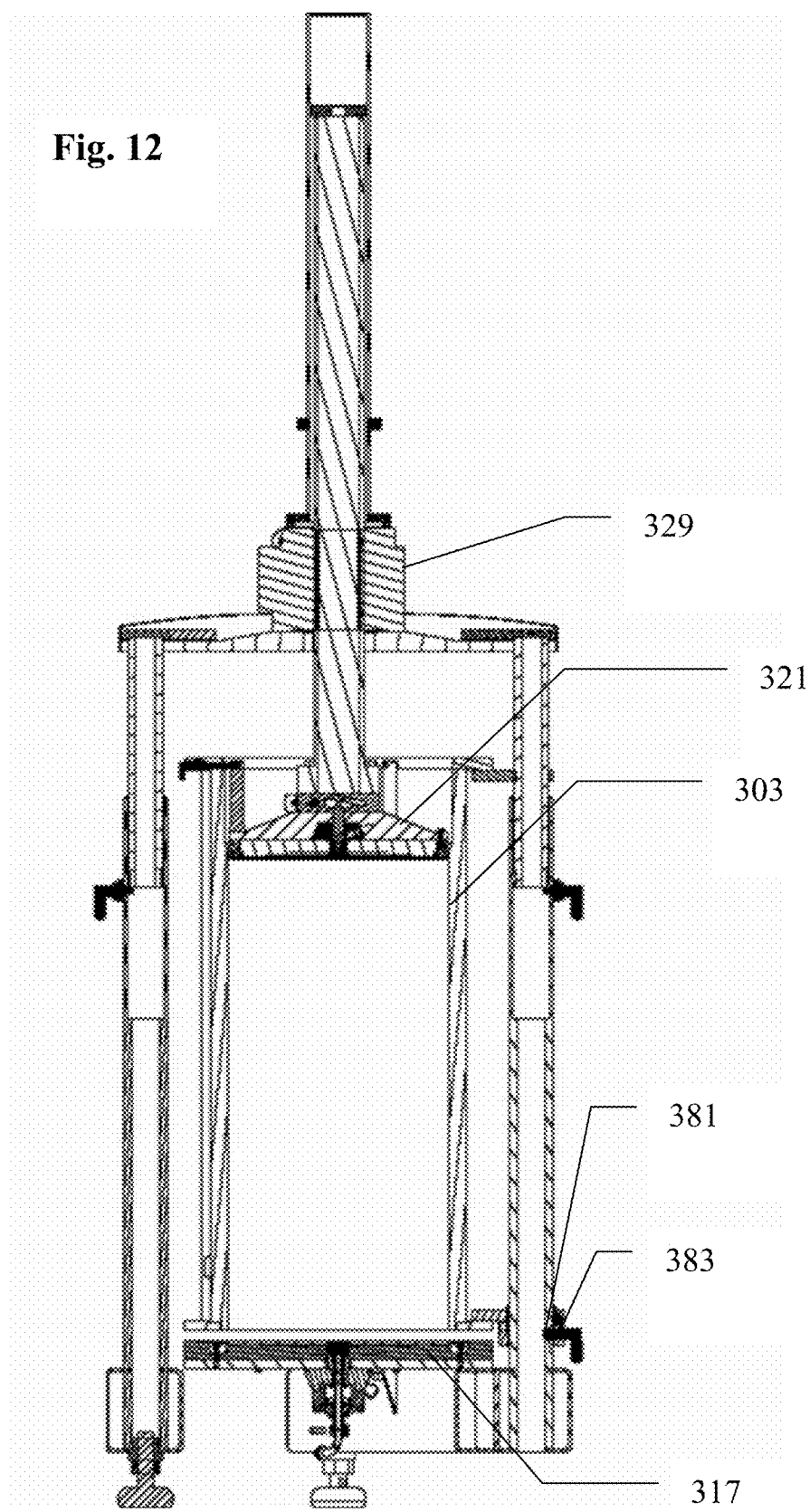

FIG. 12 shows the following stage in the method after movable adapter lifting means 329 has been actuated in the way which during normal operation would cause the movable adapter to be moved upwards. As movable adapter 321 is attached to column wall 303 this has caused column wall to be lifted off second end plate assembly 317. The movement has been continued until locking pin 383 has become aligned with locking hole 381 at which point locking pin 383 has been slid into locking hole 381. Column wall 303 is now unable to be lowered as any downward movement is prevented by the interaction of locking pin 383 on arm 353 with leg 341.

Figure 13:
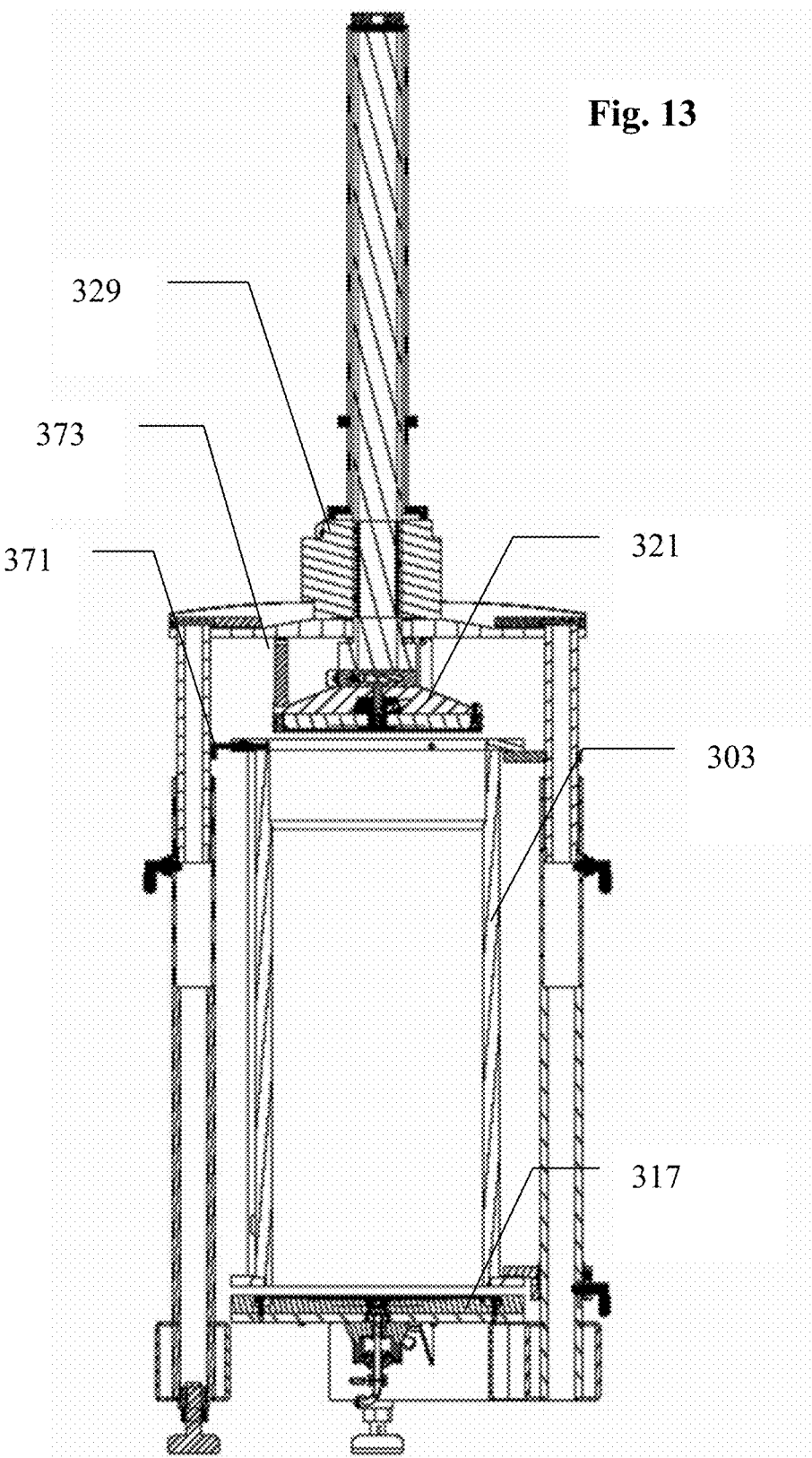

FIG. 13 shows a subsequent stage in the method in which movable adapter locking pin 371 has been moved out of engagement with locking bore 373 thereby allowing movable adapter to move relative to column wall 303. Movable adapter lifting means 329 has been actuated to lift movable adapter 321 so that none of it is inside column wall 303.

Figure 14:
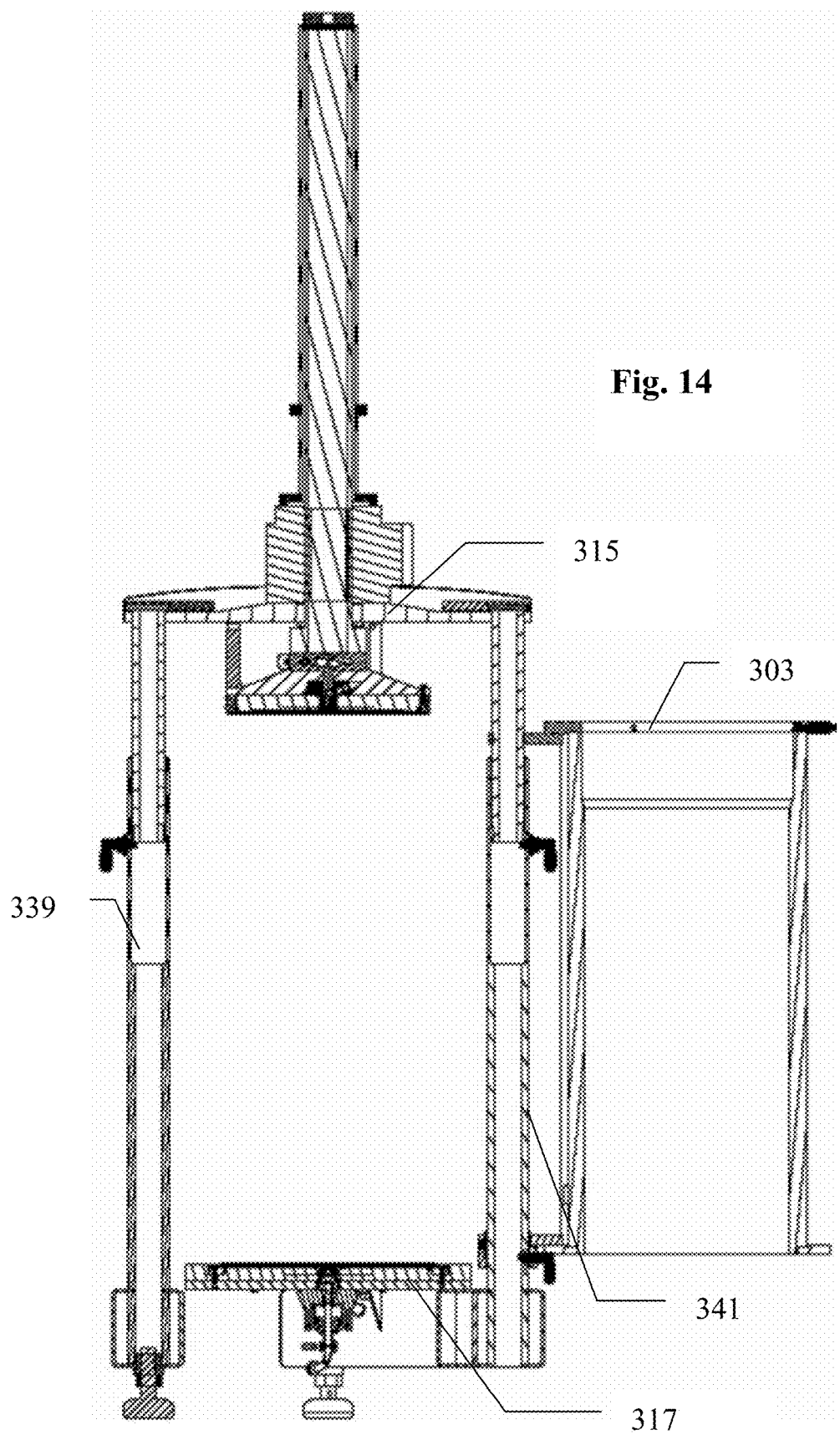

FIG. 14 shows a further stage in the method in which arms 351, 353 supporting column wall 303 have been rotated around leg 341, thereby moving column wall 303 out from between first and second end plate assemblies 315, 317.

While examples of embodiments of the present invention have been illustrated with columns using movable adapters, it is conceivable to adapt the present invention to columns which do not use movable adapters. In such cases lifting means need to be arranged to lift the first (upper) end plate assembly and column wall from the second (lower) end plate assembly, after which the column wall is prevented from being raised (e.g. by locking its supporting arms to legs in analogy with above), the fastenings between the first end plate assembly and column wall are released and the first endplate assembly raised until it is above the column wall which then may be rotated to the side. Analogously, it is also possible to adapt the present invention to columns which do not have an upper end plate assembly. In such cases the adapter must be provided with releasable locking means which can be used to lock it to the column wall in order to allow it to be used to raise the column wall off the lower end-plate.

In a further embodiment of the present invention in addition to the cylinder wall being arranged to be able to rotate about axis "1", one or more end plates are arranged to be able to rotate about axis "1".

In a further embodiment of the present invention, in addition to, or instead of, being rotatably mounted on a column leg, the arms connecting the column wall to the column leg are made telescopic in the substantially horizontal direction, thereby enabling the column wall to be moved in a straight line out from between the end plate assemblies.

While the invention has been illustrated by examples in which the vertical movements of column components are achieved using powered means, it is also possible to achieve these movements manually, for example by using brute force or any manner of lifting devices—for example, ropes and pulleys, winches, levers and jacks.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A chromatography column, having a longitudinal axis, comprising:
    a column wall with an upper first end and a lower second end;
    a first end plate assembly removably connectable to the first end of the column wall;
    a second end plate assembly removably connectable to the second end of the column wall; and
    a movable adapter, movable along the longitudinal axis from a position inside the column wall to a position outside the column wall,
    wherein the first end plate assembly, the column wall, and the second end plate assembly are arranged along the longitudinal axis, and
    wherein the column wall is rotatable about an axis of rotation is parallel to the longitudinal axis of the column and positioned outside the column.

2. The column of claim 1, further comprising a movable adapter, movable along the longitudinal axis of the column from a position inside the column to a position outside the column.

3. The column of claim 2, wherein the movable adapter is provided with means for releasably locking the movable adapter to the column wall.

4. The column of claim 1, further comprising a movable adapter lifting means for lifting the movable adapter.

5. The column of claim 1, further comprising lifting means for first end plate assembly, adapted for lifting the first end plate assembly above the column wall.

* * * * *